US 7,634,308 B2

(12) United States Patent  
Ogawa

(10) Patent No.: US 7,634,308 B2  
(45) Date of Patent: Dec. 15, 2009

(54) METHOD AND SYSTEM FOR X-RAY DIAGNOSIS OF OBJECT IN WHICH X-RAY CONTRAST AGENT IS INJECTED

(75) Inventor: Kenichi Ogawa, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 875 days.

(21) Appl. No.: 10/736,533

(22) Filed: Dec. 17, 2003

(65) Prior Publication Data

US 2004/0127789 A1 Jul. 1, 2004

(30) Foreign Application Priority Data

Dec. 17, 2002 (JP) ............... 2002-364610

(51) Int. Cl.
*A61B 6/00* (2006.01)
(52) U.S. Cl. .............. 600/431; 378/196; 378/98.12; 600/425
(58) Field of Classification Search ........... 378/62, 378/146, 195–197, 108–112, 115–116, 11, 378/12, 17, 20, 98.12, 68, 98.11; 600/425–431
See application file for complete search history.

(56) References Cited

U.S. PATENT DOCUMENTS

| | | | |
|---|---|---|---|
| 4,329,590 A | | 5/1982 | Adelmeyer |
| 4,766,603 A | * | 8/1988 | Okabe et al. ............. 378/152 |
| 5,386,450 A | * | 1/1995 | Ozawa ..................... 378/98.2 |
| 5,450,464 A | * | 9/1995 | Sakakibara .............. 378/98.2 |
| 5,870,450 A | * | 2/1999 | Khutoryansky et al. .... 378/197 |
| 5,917,882 A | * | 6/1999 | Khutoryansky et al. .... 378/116 |
| 6,052,476 A | * | 4/2000 | Qian et al. ............... 382/130 |
| 6,055,295 A | * | 4/2000 | Murthy et al. ............ 378/151 |
| 6,577,889 B2 | * | 6/2003 | Ichihashi ................. 600/425 |
| 6,764,217 B2 | * | 7/2004 | Yasuda et al. ............ 378/205 |

(Continued)

OTHER PUBLICATIONS

TH Hilbertz et al., Electro Medica (Siemens), vol. 60, No. 1, XP-000263101, pp. 2-5, "Perivision - Ein Neuer Standard Fuer Die Periphere Angiographie," 1992.*

(Continued)

*Primary Examiner*—Brian Casler
*Assistant Examiner*—Amanda L. Lauritzen
(74) *Attorney, Agent, or Firm*—Oblon, Spivak, McClelland, Maier & Neustadt, L.L.P.

(57) ABSTRACT

An X-ray diagnostic system is provided, which uses X-rays to image the lower limb of an object under conditions suitable for a flow of an X-ray contrast agent injected into the object. In the system, a C-shaped arm supports both an X-ray tube and an X-ray detector so that an object-laid tabletop is located between both the tube and the detector. For instance, one of the tabletop and the C-shaped arm is relatively moved with respect to the other so that the object is imaged along a body-axis direction thereof. The apparatus is able to perform a fluoroscopic scan to obtain a body-axis directional fluoroscopic image of the agent-injected object and to set imaging parameters, region by region in the body-axis direction, necessary for an imaging scan using the fluoroscopic image. The imaging parameters are used for the imaging scan of the agent-injected object.

18 Claims, 13 Drawing Sheets

U.S. PATENT DOCUMENTS

| | | | |
|---|---|---|---|
| 6,895,077 B2 * | 5/2005 | Karellas et al. | 378/98.3 |
| 6,990,368 B2 * | 1/2006 | Simon et al. | 600/425 |
| 2002/0041654 A1 * | 4/2002 | Hayashi | 378/196 |
| 2002/0045817 A1 * | 4/2002 | Ichihashi | 600/425 |
| 2002/0090058 A1 * | 7/2002 | Yasuda et al. | 378/205 |
| 2004/0005031 A1 * | 1/2004 | Akutsu et al. | 378/156 |
| 2005/0190983 A1 * | 9/2005 | Odogba et al. | 382/254 |
| 2006/0020198 A1 * | 1/2006 | Riederer et al. | 600/410 |
| 2006/0109954 A1 * | 5/2006 | Gohno | 378/98.12 |
| 2006/0140336 A1 * | 6/2006 | Russinger et al. | 378/4 |
| 2006/0173276 A1 * | 8/2006 | Van Den Brink et al. | 600/410 |
| 2006/0241390 A1 * | 10/2006 | Kruger et al. | 600/420 |
| 2007/0145978 A1 * | 6/2007 | Kuhara | 324/318 |
| 2007/0195932 A1 * | 8/2007 | Nakaura et al. | 378/98.12 |
| 2007/0211851 A1 * | 9/2007 | Ogawa | 378/42 |

OTHER PUBLICATIONS

U.S. Appl. No. 10/609,646, filed Jul. 1, 2003, Ogawa.

* cited by examiner

| POSITION OF C-SHAPED ARM | ROTATION ANGLE OF C-SHAPED ARM | OBLIQUE ANGLE OF C-SHAPED ARM | MOVING SPEED OF CONTRAST AGENT | MOVING SPEED OF C-SHAPED ARM | IMAGING INTERVAL | FRAME RATE | X-DIRECTIONAL POSITION OF COLLIMATOR | Y-DIRECTIONAL POSITION OF COLLIMATOR |
|---|---|---|---|---|---|---|---|---|
| $\phi 1$ | $\theta 1$ | $\theta' 1$ | $\lambda 1$ | $\beta 1$ | K1 | f1 | x1 | y1 |
| $\phi 2$ | $\theta 2$ | $\theta' 2$ | $\lambda 2$ | $\beta 2$ | K2 | f2 | x2 | y2 |
| $\phi 3$ | $\theta 3$ | $\theta' 3$ | $\lambda 3$ | $\beta 3$ | K3 | f3 | x3 | y3 |
| | | | | | | | | |
| | | | | | | | | |
| | | | | | | | | |
| $\phi n$ | $\theta n$ | $\theta' n$ | $\lambda n$ | $\beta n$ | Kn | fn | xn | yn |

FIG. 6

METHOD AND SYSTEM FOR X-RAY DIAGNOSIS OF OBJECT IN WHICH X-RAY CONTRAST AGENT IS INJECTED

BACKGROUND OF THE INVENTION

1. Technical Field of the Invention

The present invention relates to a method and system for X-ray diagnosis of an object in which an X-ray contrast agent is injected, and in particular, to the method and system preferable to an examination for angiography of a lower limb of the object.

2. Related Art

An X-ray diagnostic system is one of medial imaging modalities that can be utilized for examination and diagnosis for various regions of an object to be examined. One of the examinations carried out by the X-ray diagnostic system is lower-limb angiography of the object.

The lower-limb angiography under the X-ray diagnostic system is carried out such that an X-ray contrast agent is injected into the artery of an object at the groin portion thereof and an X-ray is scanned to track a flow of the contrast agent. Hence the scanning is carried out over a wide range from a region near to the pelvis to the tiptoes. It is difficult to obtain an entire image of such a wide range through one time of imaging, and several times of imaging is carried out to cover such a wide range. The resultant partial images are combined to form the entire image. Since this imaged range contains different parts, such as crural areas, knees, second thighs, and malleolus portions, of which sizes (widths and lengths) are different from each other, halation will occur if, for example, the second thighs are scanned on condition that a range to be X-ray radiated is assigned to a size to be fit to the pelvis. The halation, if occurring, will degrade the quality of images.

To avoid such a drawback, a conventional technique has been provided, which requires that a width-directional opening of an X-ray collimator be adjusted such that an X-ray will not be radiated outside beyond the contour of an object to be scanned.

Another conventional technique for preventing the halation has been known by Japanese Patent Laid-open publication No. 6-217973. The publication (pages 21-22 and FIG. 50) explains that the lower limb is imaged with movements of scan positions, in which a preparation scan (or pre-scan) is first performed to detect contour data of an object to be examined to positional data of a couch on which the object is laid. The detected data of the contours and positions is produced into a control table to be referred when an imaging scan is performed. Specifically, the control table is subjected to reference so that the width-directional opening of an X-ray collimator is controlled for every position of the couch, which prohibits the X-ray from being radiated outside beyond the object's contours. In contrast, in this opening control of the X-ray collimator, the length-directional opening thereof (that is, the opening in a body-axis direction of the object) is always set to a constant value.

However, an actual blood flow speed is not constant over the wide region from the pelvis to the tiptoes. In such a wide region, there are various portions in which the blood flows at slower speeds and the blood flows at faster speeds. Furthermore, such a wide region includes some portions through which blood vessels run in simple and/or complicated ways. Hence if the lower limb is imaged with the movements of scanning positions in the condition in which the longitudinal opening of the X-ray collimator (that is, the opening of the X-ray collimator in a direction along the lower limb of an object) is held constant, the resultant images suffer from having some portions that are insufficient for diagnosis.

To overcome this difficultly, it may be possible to employ a technique in which an imaging interval along the direction of the lower limb of an object is shortened to increase the number of times of imaging. Such a technique forces the longitudinal opening of the X-ray collimator to be narrowed, so that the foregoing difficulty can be improved, but an operator should accept a narrowed display area of scanned images and is obliged to track the flow of the contrast agent for imaging by using the narrower-display-area images. Hence the operations for the imaging are complicated and ballooned.

SUMMARY OF THE INVENTION

The present invention has been made with due consideration to the foregoing difficulties, and an object of the present invention is to provide an X-ray diagnostic system and an X-ray diagnostic method capable of making it possible to perform X-ray scanning in the most suitable conditions to track the flow of an X-ray contrast agent injected in an object to be examined and of lessening an operator's burden so as to improve the operationality.

In order to realize the foregoing object, according to one aspect of the present invention, there is provided an X-ray diagnostic system comprising: an X-ray source irradiating an X-ray; an X-ray detector detecting the X-ray; a support apparatus, a fluoroscopic scan unit, an imaging parameter setting unit, and an imaging scan unit. Of these, the support apparatus is configured to support both the X-ray source and the X-ray detector so that both the X-ray source and the X-ray detector are opposed to each other with a space left therebetween, a tabletop on which an object to be examined is laid being located in the space, the object being subjected to injection of an X-ray contrast agent when the object is examined. The fluoroscopic scan unit is configured to relatively move one of the tabletop and the support apparatus with respect to the other and to perform a fluoroscopic scan along a direction predetermined with respect to the object with one of the tabletop and the support apparatus relatively moved with respect to the other, the X-ray contrast agent flowing substantially along the direction, thereby a fluoroscopic image of the object being provided along the direction. The imaging parameter setting unit is configured to set, at every region to be examined of the object, imaging parameters required for an imaging scan on the basis of the fluoroscopic image, the regions being at least continuous without a gap along the direction determined with respect to the object. And the imaging scan unit is configured to relatively move one of the tabletop and the support apparatus with respect to the other and, with one of the tabletop and the support apparatus relatively moved with respect to the other, perform the imaging scan on the object on the imaging parameters set by the imaging parameter setting unit.

It is therefore possible for the X-ray diagnostic system to control an X-ray radiated filed on an object on the track of a flow of an X-ray contrast agent, whereby higher-grade X-ray radiography images are provided. In addition, an operational burden on physicians can be reduced to a great extent, thus providing the X-ray diagnostic system with improved operationality.

It is preferred that the imaging parameter setting unit is configured to accept information inputted manually by the operator and to set the imaging parameters in response to the operator's manually inputted information. For example, according to a flowing speed of the X-ray contrast agent, a relative moving speed of one of the tabletop and the support apparatus to the other can be controlled. Also the flowing speed of the X-ray contrast agent can be used for control of a frame rate for the X-ray imaging. As a result, corresponding to the flow states of the X-ray contrast agent, X-ray imaging conditions can be optimized.

It is also preferred that the imaging parameter setting unit is configured to, from the fluoroscopic image obtained by the fluoroscopic scan unit, automatically recognize the region through which the X-ray contrast agent flows and to set the imaging parameters based on a recognized result of the automatic recognition. This automatic recognition allows the flow of the X-ray contrast agent to be traced automatically during the fluoroscopic scan, so that an opening of the X-ray collimator can be adjusted substantially in real time even under the fluoroscopic scan. The automatic recognition of flow of the contrast agent provides a flowing speed and an amount of movement thereof. These pieces of information about the contrast agent are used to automatically determine imaging parameters, such as an X-ray collimating opening at each imaging position and a relative moving speed between the tabletop and the support apparatus, thus remarkably lowering an operational burden on physicians.

According to a second aspect of the present invention, there is provided a method of X-ray imaging performed by the X-ray diagnostic system comprising an X-ray source irradiating an X-ray; an X-ray detector detecting the X-ray; and a support apparatus configured to support both the X-ray source and the X-ray detector so that both the X-ray source and the X-ray detector are opposed to each other with a space left therebetween, a tabletop on which an object to be examined is laid being located in the space, the object being subjected to injection of an X-ray contrast agent when the object is examined, the method comprising the steps of: relatively moving one of the tabletop and the support apparatus with respect to the other and performing a fluoroscopic scan along a direction predetermined with respect to the object with one of the tabletop and the support apparatus relatively moved with respect to the other, the X-ray contrast agent flowing substantially along the direction, thereby a fluoroscopic image of the object being provided along the direction; setting, at every region to be examined of the object, imaging parameters required for an imaging scan on the basis of the fluoroscopic image, the regions being at least continuous without a gap along the direction determined with respect to the object; and relatively moving one of the tabletop and the support apparatus with respect to the other and, with one of the tabletop and the support apparatus relatively moved with respect to the other, performing the imaging scan on the object on the imaging parameters. This method also provides the similar or identical advantages to those provided by the X-ray diagnostic system.

BRIEF DESCRIPTION OF THE DRAWINGS

In the accompanying drawings:

FIG. 6 explains a table formed in a memory, set values indicative of imaging parameters determined through the setting operations for the imaging conditions;

DETAILED DESCRIPTION OF PREFERRED EMBODIMENTS

Preferred embodiments of an X-ray diagnostic system according to the present invention will now be described in detail with reference to the accompanying drawings.

First Embodiment

Referring to FIGS. 1 to 7, a first embodiment of an X-ray diagnostic system according to the present invention will now be detained.

The X-ray diagnostic system according to the first embodiment is equipped with a support apparatus 10, an X-ray tube 20, an X-ray detector 30 and a controller 50.

Figure 1:
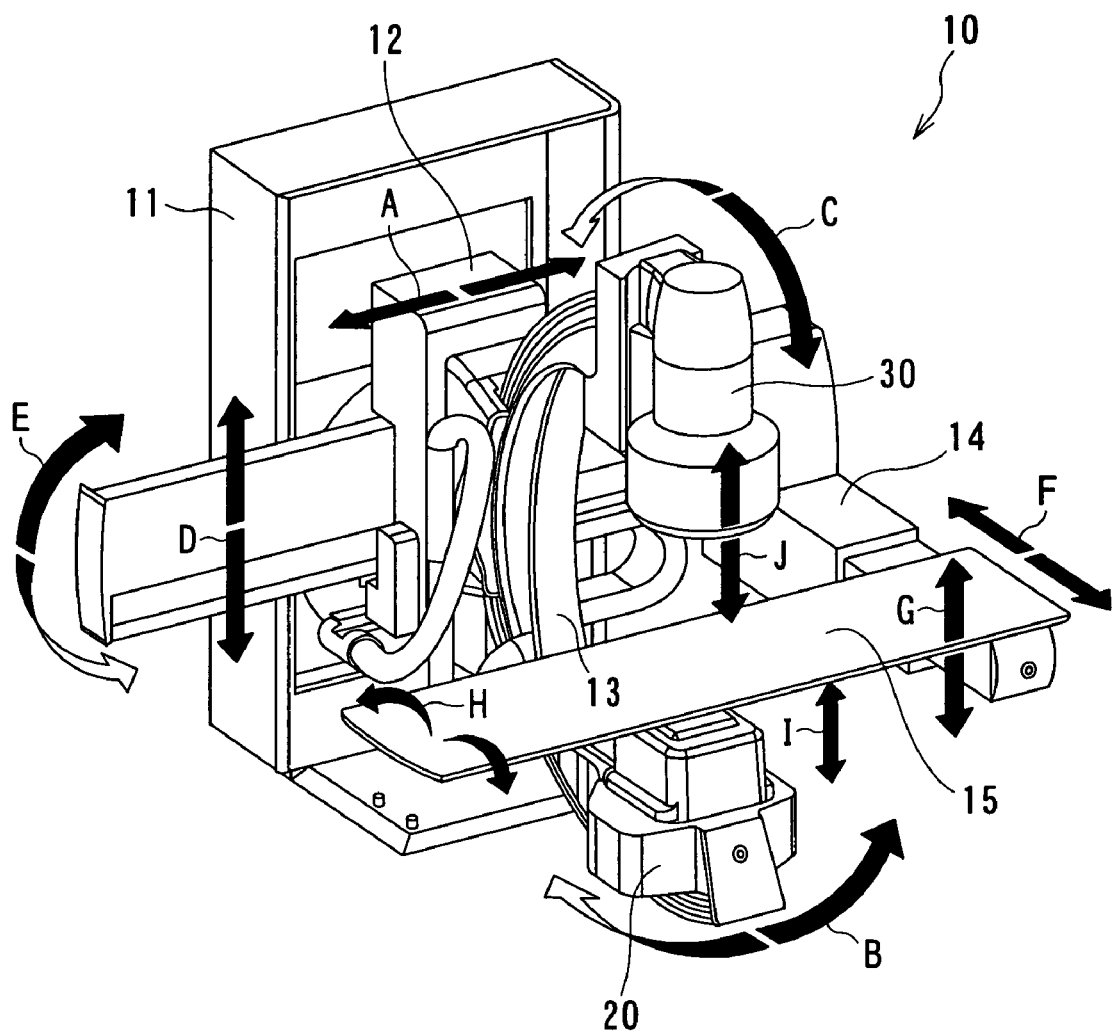
FIG. 1 is a perspective view outlining the configuration of a support apparatus of an X-ray diagnostic system according to embodiments of the present invention.

FIG. 1 is a perspective view outlining a partial configuration of the support apparatus 10 of the X-ray diagnostic system 10. This support apparatus 10 has, as the main components, a supporting main unit 11, a C-shaped arm support mechanism 12, a C-shaped arm 13, a tabletop support mechanism 14, and a tabletop 15.

The supporting main unit 11 is fixed on the floor and slidably supports the C-shaped arm support mechanism 12 in a direction approximately parallel with the floor (as shown by arrows "A" in FIG. 1). The C-shaped arm 13 is attached to the C-shaped arm support mechanism 12 such that the arm 13 is rotatable along a plane approximately perpendicular to the floor about an arm attachment position to the mechanism 12

(as shown by arrows "B" in FIG. 1) and is slidable in an arch-like direction (shown by arrows "C" in FIG. 1). As a result, the C-shaped arm 13 can be tilted to the tabletop 15 which will be described later. Though described later, both of the X-ray tube 20 and the X-ray detector 30 are secured on the C-shaped arm 13 with the tabletop 15 located therebetween.

The tabletop support mechanism 14 is supported by the supporting main unit 11 in such a manner that the mechanism 14 can be moved up and down (as shown by arrows "D" in FIG. 1) and rotated (as shown by arrows "E" in FIG. 1).

The tabletop 15 is secured on the tabletop support mechanism 14 so that the tabletop 15 is slidable in a width direction thereof (as shown by an arrow "F" in FIG. 1) is movable in a thickness direction of the tabletop 15 (as shown by arrows "G" in FIG. 1). In addition, the tabletop 15 is secured to be able to rotate about a central axis along its longitudinal direction (as shown by arrows "H" in FIG. 1). As pictorially shown in FIG. 2, a patient P (i.e., an object) to be examined is laid on the tabletop 15.

Figure 2:
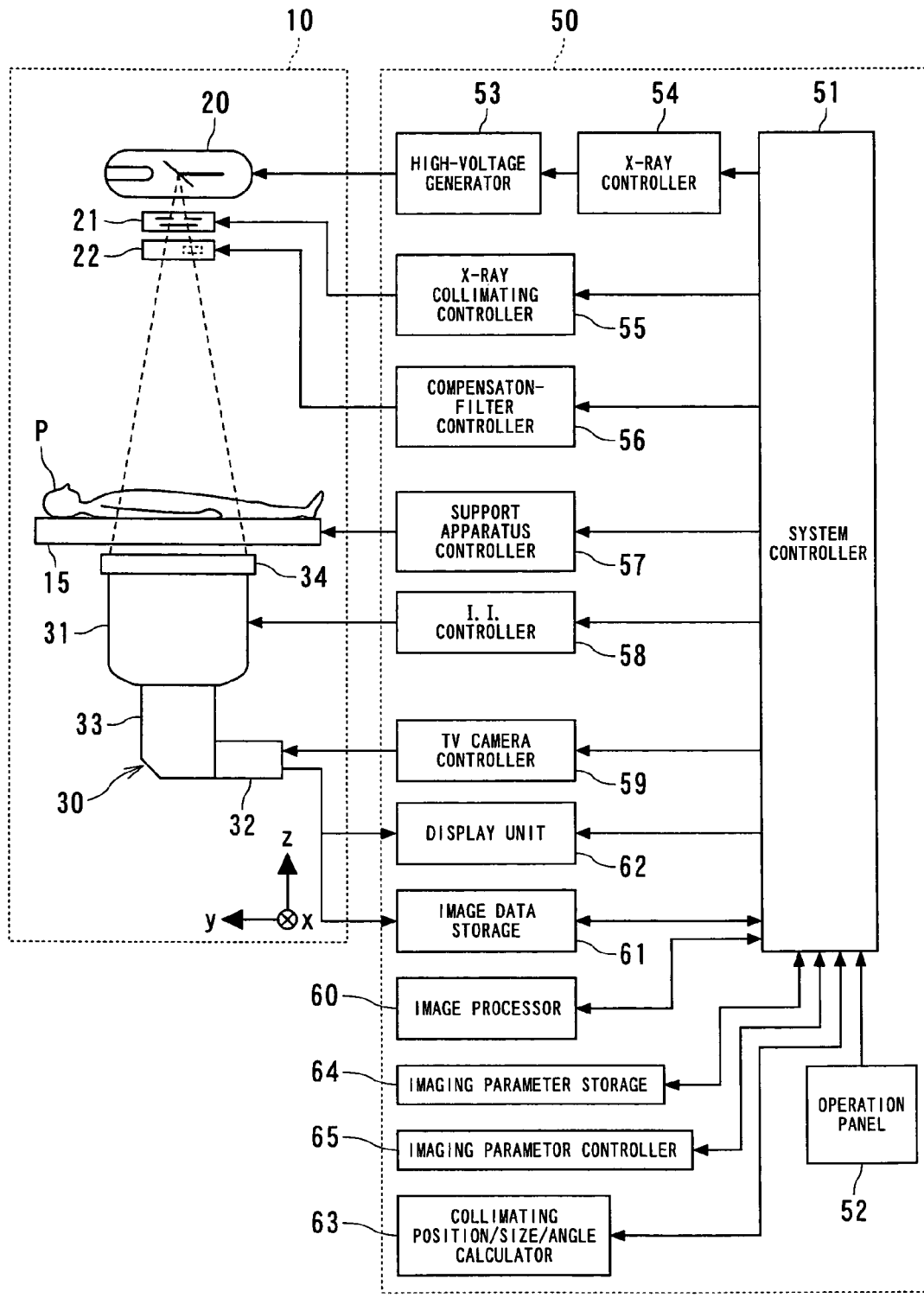
FIG. 2 is an electrical block diagram showing the X-ray diagnostic system according to a first embodiment of the present invention.
Figure 3:
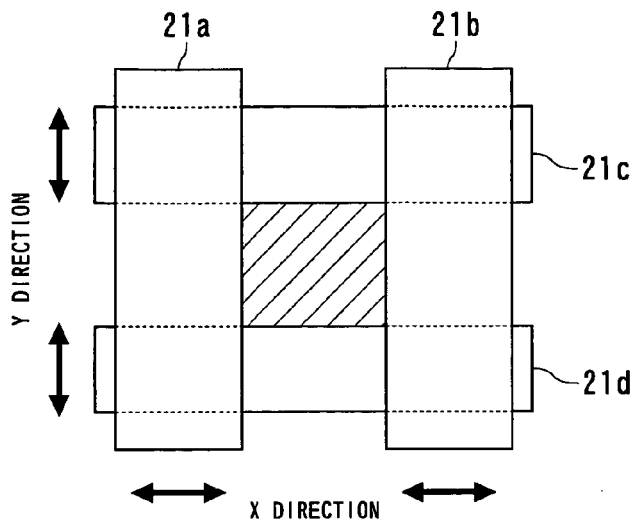
FIG. 3 is a plan view explaining operations of an X-ray collimator equipped in the X-ray diagnostic system.

On one end of the C-shaped arm 13 supported by the C-shaped arm support mechanism 12, the X-ray tube 20 is secured to face the tabletop 15. On the frontal surface of the X-ray tube 20 are provided an X-ray collimator 21 and a compensation filter 22 (refer to FIG. 2). The X-ray collimator 21 is in charge of collimating a region on the object, onto which an X-ray beam is radiated from the X-ray tube 20, into a desired one, with the result that the X-ray is prevented from being radiated onto unnecessary portions of the object. This X-ray collimator 21 is configured to, for example, as shown in FIG. 3, have plate-like collimating blades 21a to 21d made of lead and arranged in a double cross. Each of the collimating blades 21a to 21d is connected to a servo motor via a rack-and-pinion mechanism and driven by those components such that the two opposed collimating blades 21a and 21b (21c and 21d) come closer to each other or depart away from each other. Those movements of the blades are able to form a desired radiation range through which the X-ray beam passes (refer to a hatching area called "radiation field" or "collimating opening").

The compensation filter 22 is used to attenuate the amount of the X-ray in part in an X-ray radiation range.

The X-ray tube 20, X-ray collimator 21, and compensation filter 22 are secured so that they can move back and forth from and toward the tabletop 15 at the one end of the C-shaped arm 13 (as shown by arrows "I").

Furthermore, on the other end of the C-shaped arm 13, the X-ray detector 30 is secured to be opposed to the X-ray tube 20 via the tabletop 15. By way of example, as shown in FIG. 2, this X-ray detector 30 is provided with an image intensifier (hereinafter referred to as I.I.) 31 and a TV camera 32 with an imaging tube or a solid imaging device (such as CCD: Charge Coupled Device), and an optical system 33 placed to combine both the I.I. 31 and the TV camera 32. An X-ray grid 34 is placed on the front of the I.I. 31 (that is, on the plane of the I.I. 31 that faces the tabletop 15). The I.I. 31 receives X-rays transmitted through an object P after being radiated from the X-ray tube 20, and converts the received X-rays into an optical image. This optical image is made to enter the TV camera 32 via the optical system 33 to be converted to a TV video signal. The X-ray grid 34 is responsible for preventing scattered X-rays caused in the object P from entering the I.I. 31. The X-ray detector 30, which is constructed as above, is configured to be movable in a direction coming closer to the tabletop 15 and returning to the C-shaped arm 13, as shown by arrows J in FIG. 1.

The controller 50, which is one of the main constituents of the present X-ray diagnostic apparatus and comparable to the support apparatus 10, will now be explained in connection with FIG. 2. FIG. 2 is a system diagram showing the devices composing the controller 50, besides both the X-ray tube 20 and X-ray detector 30 attached to the support apparatus 10.

The controller 50 comprises a system controller 51, an operation panel 52, a high-voltage generator 53, an X-ray controller 54, an X-ray collimating controller 55, a compensation-filter controller 56, and a support-apparatus controller 57.

Of these components, the system controller 51 plays a centric role for integrally controlling the entire operation of the X-ray diagnostic apparatus. The operation panel 52 is provided with a keyboard and/or a touch panel and a pointing device such as mouse and track ball, which are used by an operator to give commands to the system controller 51. The high-voltage generator 53 generates a high-voltage signal to be applied to the X-ray tube 20. The X-ray controller 54 controls the operation of the high-voltage generator 53.

Furthermore, the X-ray collimating controller 55 is to control amounts to be moved of the collimating blades 21a to 21d, which give a desired X-ray radiation field, that is, a desired opening of the X-ray collimator 21. The compensation-filter controller 56 is designed to control positions and others of the compensation filter 22. The support-apparatus controller 57 is mainly in charge of controlling the operations of both the C-shaped arm support mechanism 12 and the C-shaped arm 13 supported by the mechanism 12 as well as the operations of both the tabletop support mechanism 14 and the tabletop 15 supported by the mechanism 14.

The controller 50 is still provided with an I.I. controller 58 controlling the operation of the I.I. 31, a TV camera controller 59 controlling the operation of the TV camera 32, an image processor 60, an image data storage 61, an image processor 60, and a display unit 62. The image data storage 61 is placed to memorize data of images acquired by the TV camera 32 and processed by the image processor 60, together with X-ray control conditions required by the X-ray controller 54, X-ray collimating controller 55, and compensation-filter controller 56, data of imaging realized by the support-apparatus controller 57, image processing conditions required by the image processor 60, and others.

Furthermore, the image processor 60 is configured to apply various types of processing, such as gradation processing, spatial filtering, addition, and/or subtraction, to image data read out from the image data storage 61 and/or image data acquired in real time from the TV camera 32. The display unit 62 is placed for real-time visualization of images acquired by the TV camera 32 and/or display of images processed by the image processor 60.

The controller 50 is still provided with a collimating position/size/angle calculator 63, an imaging parameter storage 64, and an imaging parameter controller 65. Of these the collimating position/size/angle calculator 63 uses the data of an image stored in the image data storage 61 so that data indicative of a collimating position, size and angle appropriate for the image is calculated in the form of graphic data on the basis of a positional signal from the X-ray collimating controller 55 when the image is acquired.

The imaging parameter storage 64 calculates, for a plurality of regions, movement speeds appropriate for the C-shaped arm 13 on the basis of information about both movement points to be interest of an X-ray contrast agent and imaging positions and memorizes the calculated results together with the position and size of the collimator and a temporal interval for imaging.

The imaging parameter controller 65 is responsible for controlling the X-ray collimating controller 55, support-apparatus controller 57, and others using positional information and a specified imaging sequence so that the C-shaped arm 13 is moved at a proper speed. Such proper speeds are stored, imaging sequence by imagining sequence, in the imaging parameter storage 64.

Figure 4A:
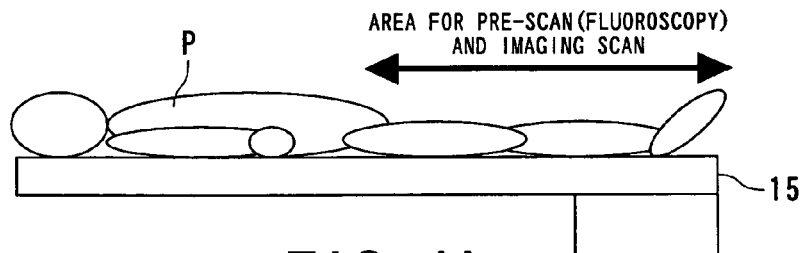
FIG. 4A is an illustration showing an imaging area subjected to both a pre-scan and an imaging scan.
Figure 4B:
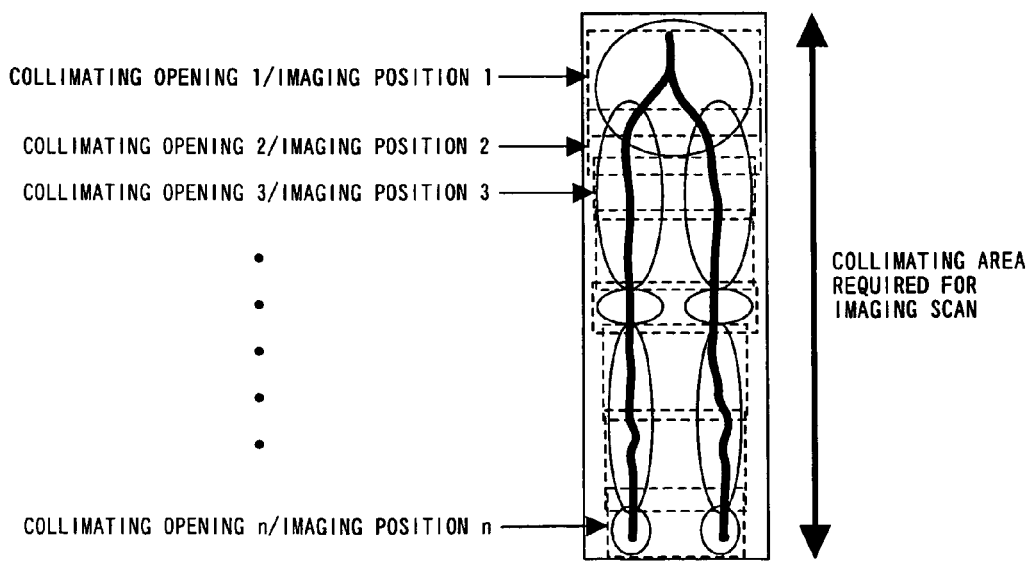
FIG. 4B explains how to manually set an opening of the X-ray collimator at each imaging region in the first embodiment.

The operation of the above-configured X-ray diagnostic apparatus will now be explained in the case that the apparatus performs lower-limb angiography. In FIGS. 2, 4A and 4B, the three mutually-orthogonal directions are defined such that a width direction of an object P to be examined who is laid on the tabletop 15 is an X-direction, a body-axis direction of the object P is a Y-direction, and a thickness direction of the object P is a Z-direction.

First, fluoroscopic imaging involving the injection of an X-ray contrast agent is carried out over a wide area from the pelvis region to the tiptoes of an object P to be examined and an opening of the X-ray collimator 21 is determined at every region of the object P. That is, the fluoroscopic imaging is carried out as a pre-scan that uses the contrast agent. In this fluoroscopic imaging, a small quantity of X-ray contrast agent is bolus-injected into the lower limb of an object to be examined and a lower-strength of X-ray is radiated toward the object so that X-ray transmission data for positioning for a main scan can be acquired.

Since one time of scanning is almost impossible to provide an entire image of a desired region to be diagnosed, the scanning is performed part by part, with the tabletop 15 kept stationary, as the C-shaped arm 13 (i.e., both the X-ray tube 20 and the X-ray detector 30) is moved along the longitudinal direction of the tabletop 15 (i.e., the Y-direction). Hence several pieces of partial images are obtained, and then connected to the entire image of the lower limb. The C-shaped arm 13 is moved by making the C-shaped arm support mechanism 12 travel along the directions of the arrows "A" in FIG. 1 under the operation of the support-apparatus controller 57. To enable a desired region of the object to be depicted at the highest image quality, a rotation angle and/or an oblique angle of the C-shaped 13 with respect to the tabletop 15 can be designated as desired angular amounts (refer to the directions shown by the arrows B and C in FIG. 1).

FIG. 4A employs arrows to outline a partial range of an object P subjected to X-ray imaging in cases where the lower-limb contrast angiography is performed. FIG. 4B shows a long image of the entire lower limb, made by connecting partial images previously acquired through the fluoroscopic imaging. On the entire lower-limb image, as shown in FIG. 4B, an opening of the X-ray collimator 21 is given every region, the openings being for the main scan.

Specifically, first of all, an X-ray contrast agent is injected to an object P to be examined, and as shown in FIG. 4A, an area shown by the arrows is subject to several times of fluoroscopic imaging, thereby providing a fluoroscopic image every time of imaging. The resultant fluoroscopic images are then stored in turn into the image data storage 61. Then under the control of the system controller 51, the fluoroscopic image data is read out image by image from the image data storage 61, and then sent to the image processor 60 where the data of respective images undergoes the mutual connection to form an entire image. As a result, as shown in FIG. 4B, the entire image of the lower limb is displayed as a long-plate image on the display unit 62.

On the long-plate-like fluoroscopic image or a fluoroscopic image of each imaging area to be interest on the display unit 62, an operator uses the pointing device on the operation panel 52 to set, every region divided arbitrarily, to the image, a desired size of the X-ray collimator 21 which will be appropriate for the main scan. In other words, over the wider area from the pelvis region to the tiptoes, depending on a region of particular interest, the size of each region, the flow condition of the contrast agent, and/or others, both an imaging position (areal position) and a collimating opening (i.e., a region to be imaged) at each imaging position are defined as shown by dotted rectangular in FIG. 4B.

Practically, in the case of FIG. 4B, the opening of the X-ray collimator 21 is defined as "1" at an imaging position "1". At the next imaging position "2," the opening of the X-ray collimator 21 is defined as "2," and at the next imaging position "3," the opening of the X-ray collimator 21 is defined as "3," and so on (that is, at the imaging position "n" the opening of the X-ray collimator 21 is defined as "n"). It is not always true that the openings 1, 2, 3, . . . , n of the X-ray collimator 21 are different from each other, but one may be the same amount as others depending on imaging positions.

Concerning adjacent imaging positions, it is preferred that, if taking a reduced amount of object's X-ray exposure into consideration, an overlap between their imaging fields is made as small as possible in the object's body-axis direction (the Y-direction). In contrast, to track the X-ray contrast agent in motion within images without fail, a limited amount of overlap between two adjacent imaging fields is unavoidable, even when an imaging rate "f" is adjusted in dependence upon a speed λ of the contrast agent (the imaging rate is 30 frames per second at the maximum, but if necessary, can be adjusted to 15 frames per second or 7.5 frames per second, for instance).

In this way, the respective collimating openings are decided at the respective imaging positions through the operator's manual operations involving the use of the pointing device. In response to setting the collimating openings, the collimating position/size/angle calculator 63 calculates amounts to be moved of the blades 21a to 21d of the X-ray collimator 21 in both the X- and Y-directions. Data of calculated results is stored into the imaging parameter storage 64.

Figure 5:
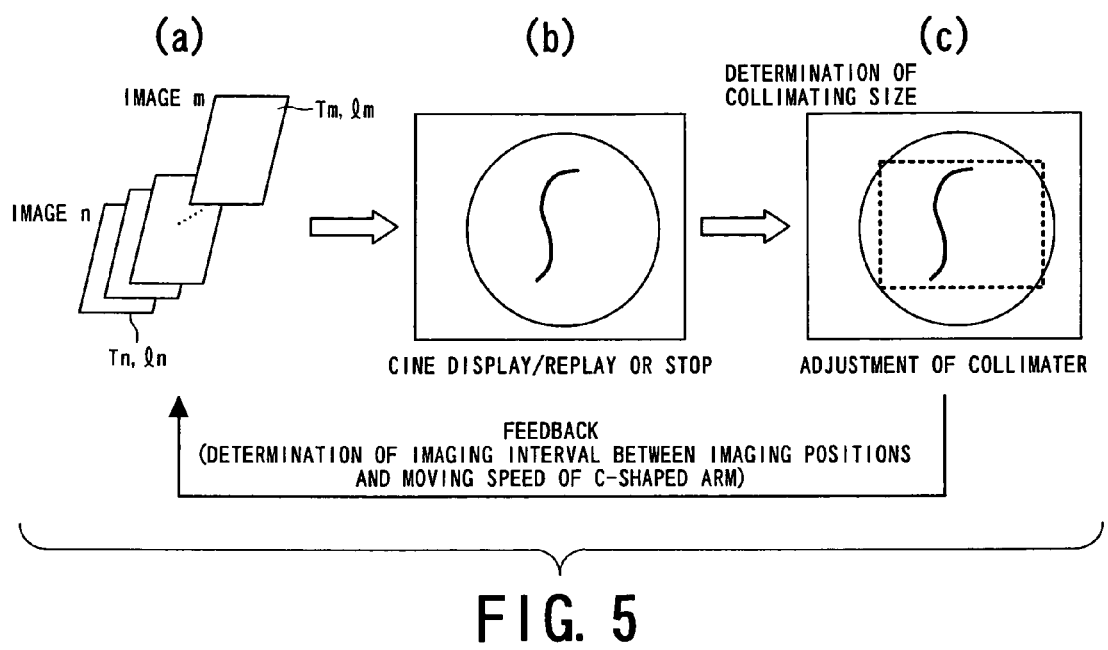
FIG. 5 explains one example of how to set a proper imaging condition at each imaging region in the first embodiment.

A plurality of X-ray fluoroscopic images, which is acquired in advance by fluoroscopic acquisition under a pre-scan to be carried out before an imaging scan, is read out from the image data storage 61 to display the fluoroscopic images in a tracing manner. As shown in FIG. 5, a feed-back flow is used to the tracing display and its processing, in which various imaging parameters including both a frame rate "f" and movement speeds of the C-shaped arm 13 can be determined according to flowing speeds of an X-ray contrast agent injected into the lower limb of the object P.

A detailed explanation will be given in FIG. 5. Plural fluoroscopic images are acquired in advance with the X-ray contrast agent injected into the object, and data of the resultant fluoroscopic images is stored in the image data storage 61, which is pictorially depicted in FIG. 5(a). Such fluoroscopic images are displayed on the screen of the display unit 62 as a cine image or a tracing image at a predetermined frame rate, as shown in FIG. 5(b). Incidentally, FIG. 5(a) pictorially shows plural frames of images from the m-th frame to the n-th frame, all of which are stored in the image data storage 61. An assumption is made such that the m-th frame image was acquired at an imaging position "lm" for an imaging period "Tm," while the n-th frame image was acquired at an imaging position "In" during an imaging period "Tn," on condition that the "m" and "n" are defined to be m<n and a frame rate "f" is 30 fps.

An operator thus displays the fluoroscopic images on the display unit 62 in sequence, as shown in FIG. 5(b), during which time the operator observes how the injected contrast agent flows in each image. When a desired image appears on the display unit 62, the replay on the screen is stopped to freeze the image. As shown in FIG. 5(c), a dashed-line frame showing an opening of the X-ray collimator 21 is placed on the frozen image, the dashed-line frame being set to an appropriate size and position for an imaging scan to be carried out after the pre-scan and limiting the X- and Y-directional positions of the blades 21a to 21d. In response to operator's operations of the pointing device on the operation panel 52, the X-ray collimating controller 55 is activated to enable the above setting operations.

As a result, an interval between frames of peak-traced images is "m to n," so that, using positional information ln and lm about the specified two points and temporal elapse information Tn and Tm based on the frame rate "f," a moving speed λ of the X-ray contrast agent is given by the following formula (1).

$$\lambda = (ln - lm)/(Tn - Tm) \quad (1)$$

In cases where the moving speed A is faster than a moving speed of the C-shaped arm 13 under the imaging scan, there is a possibility that the top position of flow of the contrast agent becomes outside the image (in this case, the image fails to trace the flow of the contrast agent). To avoid such situations, the opening of the X-ray collimator 21 in the Y-direction is reset to a large amount or the frame rate "f" is reset to a high value. By resetting such a factor, a physician is able to specify a region to be particularly interested for a physician and image the entire region that shows how the contrast agent passes therethrough.

In setting the opening of the X-ray collimator 21, an error Δ is automatically added to the opening, the error being a margin for continuously connecting the images each defined by the opening of the X-ray collimator 21 at each imaging position when the entire area to be scanned is displayed in a long sheet-like image. In addition, the pieces of information indicative of the temporal elapse times Tm and Tn and the imaging positions lm and ln are used as aid information for deciding the imaging interval "K" between imaging positions and the frame rate "f."

Sequentially repeating the foregoing operations at each of imaging regions (i.e., imaging positions) allows various imaging parameters (set values) to be set at each of the imaging positions (i.e., at each Y-directional position of the C-shaped arm 13 which is determined in relation to the tabletop 15) over the entire desired imaging area. The imaging parameters include a variety of set values, such as positions, rotation angles, oblique angles and speeds of the C-shaped arm 13, and speeds of the X-ray contrast agent. The imaging parameters are stored into the imaging parameter storage 64 in the form of a data table shown in, for example, FIG. 6.

In response to the decision of the imaging parameters such as the collimating openings, imaging intervals between imaging positions, and moving speeds of the C-shaped arm 13 at the respective imaging positions, an imaging scan for acquiring images to be actually diagnosed is performed. The imaging scan consists of a scan based on a mask sequence, which is carried out before injecting the X-ray contrast agent into an object to be imaged and a scan based on a contrast sequence, which involves the X-ray contrast agent to be injected for the scan.

Specifically, the scan on the mask sequence is carried such that, under the control of the imaging parameter controller 65, an object in which the X-ray contrast agent yet to be injected is subjected to the scan on the mask sequence under the imaging parameters decided using the foregoing fluoroscopic image acquired by the pre-scan. That is, imaging the lower limb of the object at each imaging position is shifted from its pelvis portion to the tiptoes, so that a mask image of each region is produced at each imaging position and its data is stored, together with its positional information, into the image data storage 61.

After this, an X-ray contrast agent is injected to the object, and a scan based on the contrast sequence is carried out toward the object along a direction of flow of the contrast agent under the control of the imaging parameter controller 65. This scan is done in the same way as the scan based on the mask sequence, thereby a contrast image being produced at each imaging position. In the imaging scan, both the imaging parameters such as a moving speed of the C-shaped arm 13 and information about an elapsed time counted after the injection of the contrast agent is supplied to the imaging parameter controller 65 in sequence. Thus, the imaging parameter controller 65 is allowed to perform the imaging according to the conditions read out from the imaging parameter storage 64.

When the contrast images have been acquired at the respective imaging positions, the image data is stored, together with their positional information, into the image data storage 61. Moreover, the image processor 60 works in such a manner the processor reads out the previously acquired mask images from the image data storage 61 and performs subtraction between the contrast image data and the read-out mask image data to obtain data of a difference image (subtraction image) at each imaging position. The data of the difference images at the respective imaging positions are then stored, together with information about the imaging positions, into the image data storage 61 and displayed in real time on the display unit 62. The contrast images and the mask images, which are subjected to the subtraction, are acquired from, of course, the same region of the object. Each of the difference images presents only a path through which the contrast agent passed, with the background image removed thanks to the subtraction.

In this way, in performing the imaging scan, a variety of types of set values (i.e., imaging parameters) are read out from the imaging parameter storage 64, and, under the control of the system controller 51, used to obtain both the mask images and the contrast images in compliance with the set values. It is therefore possible to produce an image proper for diagnosis every imaging region along the object's lower limb, thus an operational burden on the operator being lessened to a great degree.

Figure 7:
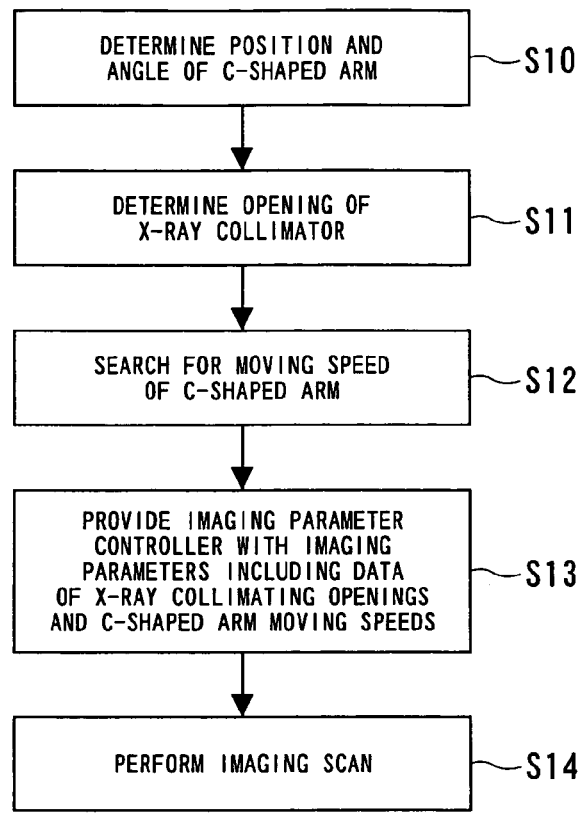
FIG. 7 is a flow chart exemplifying imaging procedures for a desired area of an object to be examined, the imaging procedures including operator's manual operations.

Referring to FIG. 7, the operations in this embodiment will now be summarized.

At step S10, the angle and position of the C-shaped arm 13 are first set to their initial values. Practically, the angle and position of the C-shaped arm 13 to the tabletop 15 are detected, and the detected values are subjected to whether or not they are shifted from their initially set values. If there are some shifts, the support-apparatus controller 57 works to correct such shifts. A command for the correction is issued from the system controller 51.

After the correction of the angle and position of the C-shaped arm 13, the processing proceeds to step S11, where the set values stored in the imaging parameter storage 64 (as shown in FIG. 6) is searched for an opening of the X-ray collimator 21 (i.e., X- and Y-directional positions of all the blades 21a to 21d) at the current imaging position. Data of the searched opening is used by the X-ray collimating controller 55, with the result that the opening of the X-ray collimator 21 is set to the specified one. This setting operation is also done under the control of the system controller 51.

Then, the processing is shifted to step S12, where the set values in the imaging parameter storage 64 are subjected to search for a moving speed β of the C-shaped arm 13 at the current imaging position. At step S13, the data of both the opening of the X-ray collimator 21 and the moving speed β of the C-shaped arm 13 are then transmitted to the imaging parameter storage 65. Accordingly, at step S14, based on the set values in the imaging parameter storage 64, the imaging parameter controller 65 works such that both the mask images and the contrast images are produced through the imaging scan.

By the way, when obtaining the contrast images in the imaging scan, an operator is allowed to keep on pushing an imaging button (not shown) on the operation panel 52, during which time the operator observes the contrast images displayed in real time on the display unit 62. Such a pushing operation enables the C-shaped arm 13 to move to follow the flow of the contrast agent in an automatic fashion, so that the contrast images are acquired during the pushing operation. In cases where the automatic tack for the contrast agent is disturbed due to some reasons, a joystick or any other operation means (not shown) on the operation panel is manually operated instead of the foregoing button, thus the C-shaped arm 13 being switched to a manual operation to follow the contrast agent. In this case, only the X-ray collimator 21 is still automatically operated.

Hence, in the present embodiment, an operational burden on the operator is relieved largely and there is provided an X-ray diagnostic system with highly improved operationality.

Figure 8:
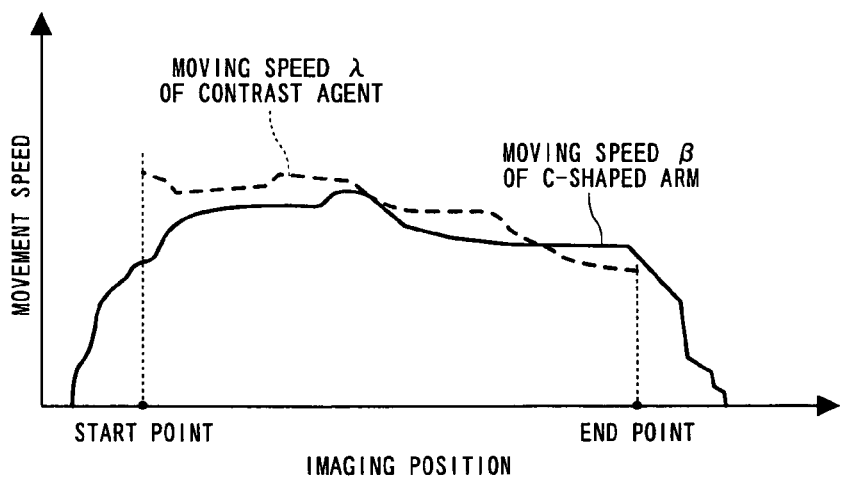
FIG. 8 explains, in the first embodiment, a function for displaying profiles of movement speeds of an X-ray contrast agent and a C-shaped arm.

There can be provided a modification, which is concerned with, as shown in FIG. 8, the display of a profile between relationships of the positions of the C-shaped arm 13 and the moving speeds of the contrast agent and the C-shaped arm 13. This profile display can be done based on information from the data table in the imaging parameter storage 64 (refer to FIG. 6), thereby effectively making use of the imaging parameters to provide another kind of diagnostic information.

Figure 9:
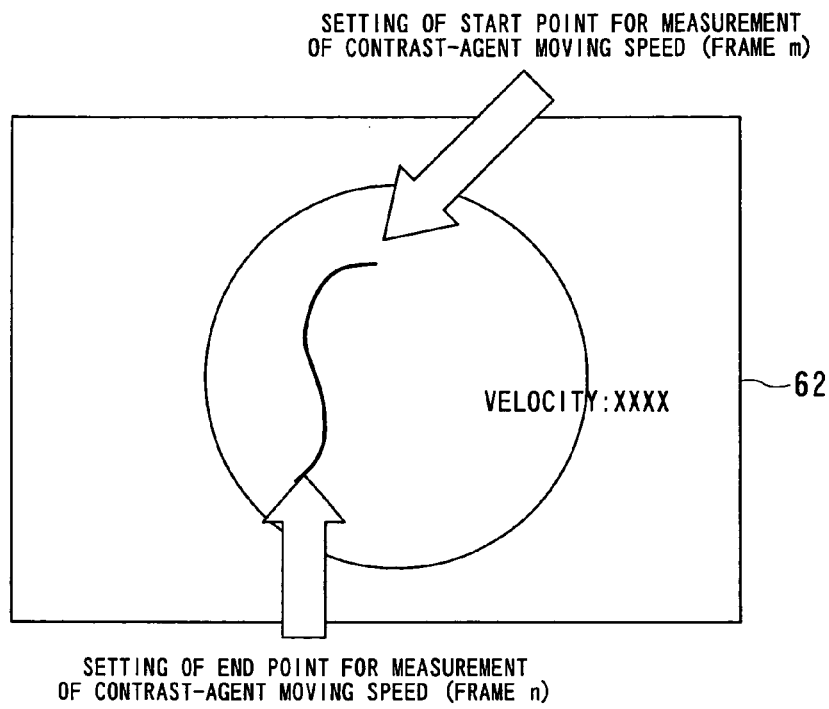
FIG. 9 explains another function for determining a movement speed of the X-ray contrast agent.

Another modification is illustrated by FIG. 9, in which an image useful for diagnosis is read out from the images stored in the image data storage 61 and subjected to cine display on the display unit 62. Both a measuring start point and a measuring end point of the X-ray contrast agent can also be overlaid on the cine displayed image and data indicative of a measured moving speed of the contrast agent or any other type of necessary information is also shown on the cine displayed image. This way of display is able to timely provide a physician with information useful for diagnosis.

Figures 10A, 10B:
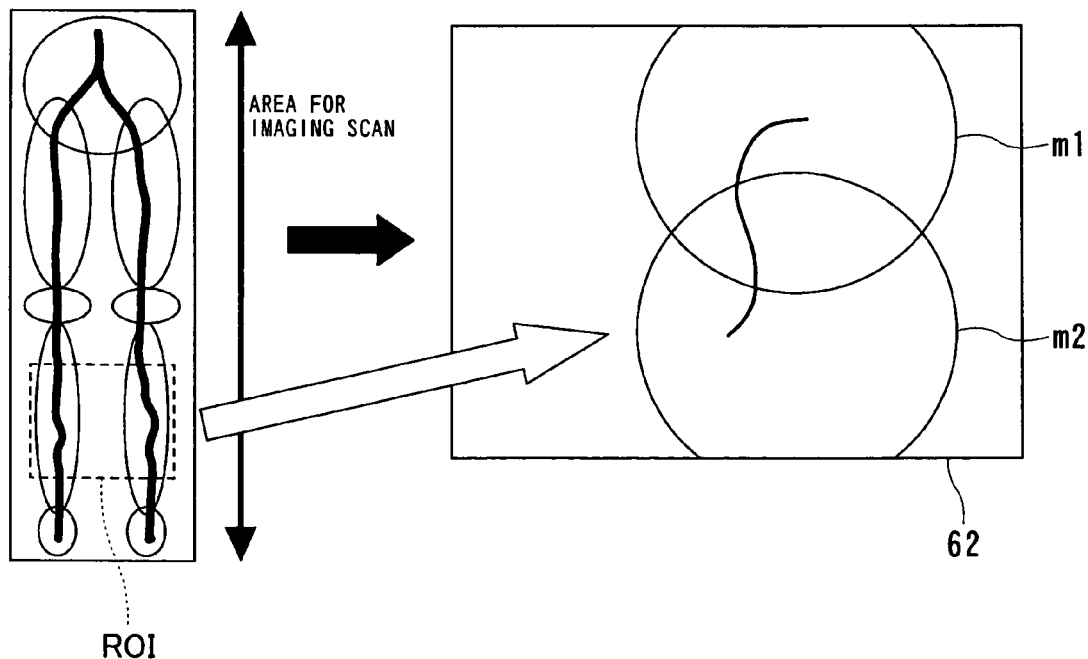
FIGS. 10A and 10B still explain another function for determining a movement speed of the X-ray contrast agent.

Still another modification can be provided with reference to FIGS. 10A and 10B. As shown in FIG. 10A, a pointing device on the operation panel 52 is used to arbitrarily place a region of interest (ROI), which makes it possible to read out data of a difference image corresponding to the region specified by the ROI from the image data storage 61, and to display the read-out image on the display unit 62. Even if the read-out image, which is specified by the ROI, is made up of a plurality of images m1 and m2, those images m1 and m2 can be connected and displayed on the display unit 62, as shown in FIG. 10B. In this display configuration, information about a moving speed of the contrast agent or others can be displayed in an overlay manner.

By the way, because blood vessels in the joint portions such as knees and malleolus portions are branched, the speed of flow of such a branched blood vessel is slower than that of the straight portions such as crural areas and second thighs. Hence, there has been known that the flow of the X-ray contrast agent is also made slower in the joint portions. Accordingly, if such joint portions are particularly interested for observation, such portions can be specified in advance. When the X-ray imaging position reaches such a specified position, the X-ray collimating controller 55 is configured to control the X-ray detector 21 such that the opening thereof (for instance, a narrower opening) proper for imaging the contrast agent of which flow speed is slower at the specified position (region). This control manner is more effective in reducing an operational burden on operators.

In order to specify such a particularly interested region, a pointing device on the operation panel 52 is also used to place, at a desired region, a ROI showing the particularly interested region. Information about this placement is stored in the imaging parameter storage 64 via the system controller 51. When the imaging parameter controller 65 operates to allow the thus-set information to be read out from the storage 64, the read-out information is sent to the X-ray collimating controller 55 via the system controller 51. As a result of it, the opening of the X-ray collimator 21, that is, an X-ray radiated field, is adjusted to an optimum size according to the read-out information at the region of interest. This field control is helpful for lessening an amount of X-ray exposure, with an operational burden reduced.

Instead of the foregoing technique, the C-shaped arm arrives at a region where the contrast agent flows relatively slowly, the frame rate can be lowered to further relieve an X-ray exposure amount.

Second Embodiment

Referring to FIGS. 11 to 16, a second embodiment of the X-ray diagnostic system according to the present embodiment will now be described. The present second embodiment features that the routine to set imaging parameters for the imaging scan using a fluoroscopic image acquired through the pre-scan can be automated, not manually performed by an operator.

Figure 11:
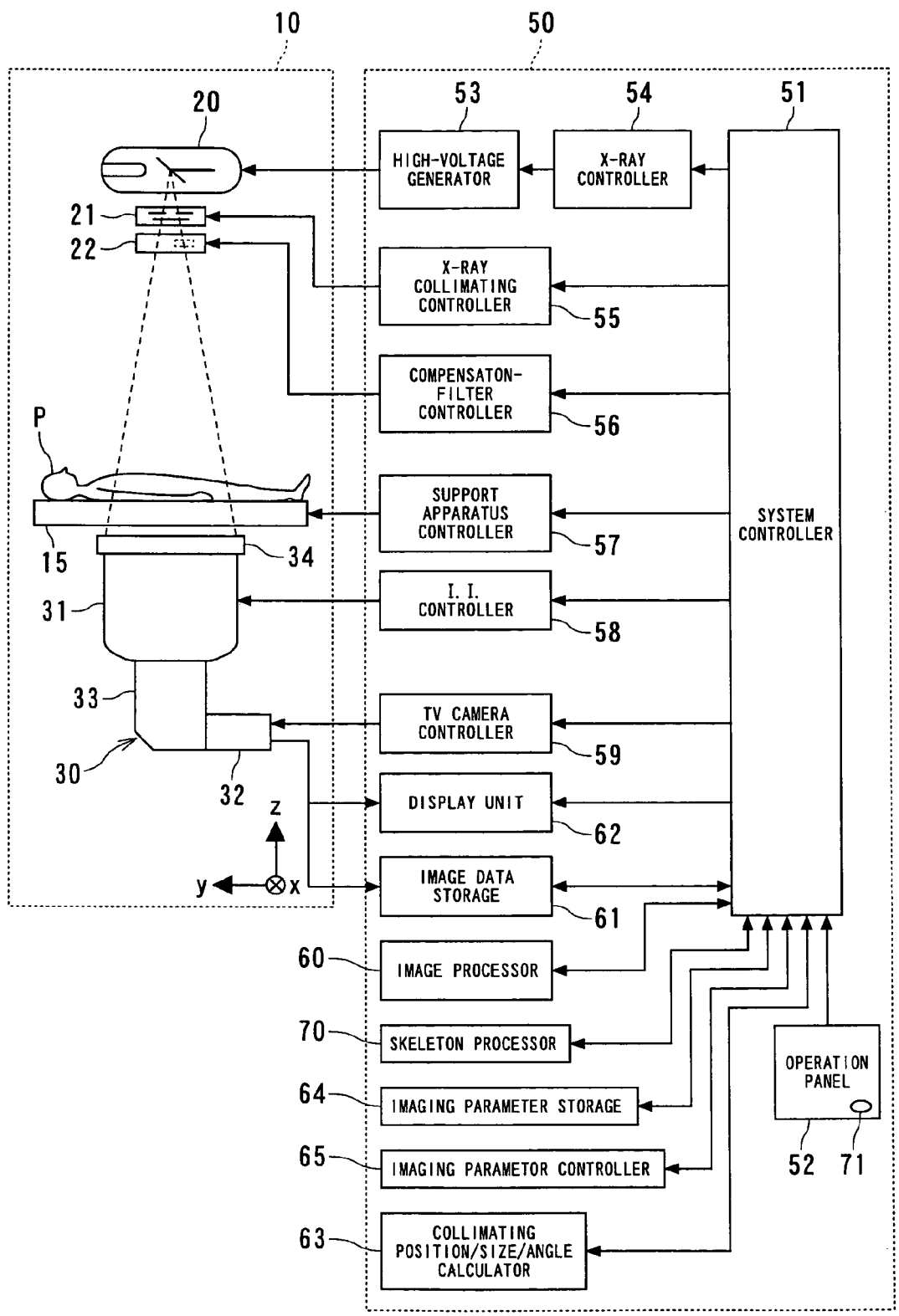
FIG. 11 is a block diagram showing an outlined electrical configuration of an X-ray diagnostic system according to a second embodiment of the present invention.

In order to automatically set the imaging parameters, the X-ray diagnostic system according to the second embodiment is newly provided, as shown in FIG. 11, with a skeleton processor 70 to extract and process skeletons as patterns of the X-ray contrast agent injected in an object. In addition, the operation panel 52 is equipped with a dead man's switch 71 as an additional switch. The remaining hardware configurations are identical or similar to those used by the first embodiment.

The skeleton processor 70 is provided as a processor of which main configuration is a computer equipped with a CPU and memories for memorizing programs, for computation, and for memorizing data, though they are not shown.

When the skeleton processor 70 is activated, programs previously stored in the program memory are read out into the computing memory, and the processing is performed in accordance with the predetermined procedures described in the programs. The processing is outlined in FIG. 12.

Figure 12:
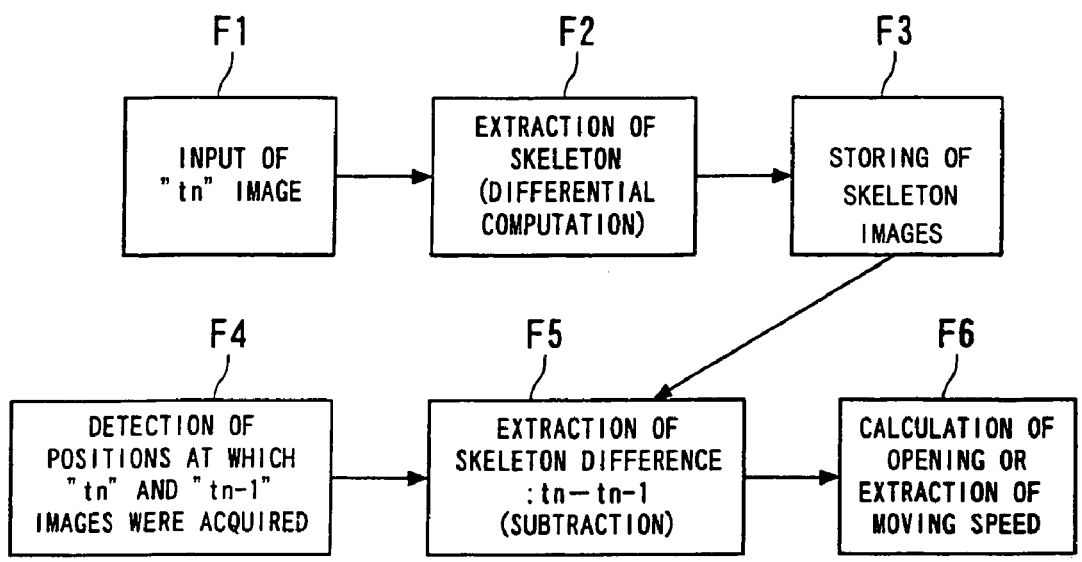
FIG. 12 is a functional block diagram outlining processing carried out by a skeleton processor employed by the X-ray diagnostic system in the second embodiment.

In other words, as shown in FIG. 12, the processing functionally realizes various components. These components includes an image input unit F1, skeleton extraction unit F2, storing unit F3, detecting unit F4, difference extraction unit (difference circuit) F5, and processing unit F6. Of these units, the image input unit F1 inputs image data acquired by the pre-scan. The skeleton extraction unit F2 performs differential processing to extract a pattern of the X-ray contrast agent (hereinafter referred to as skeleton). Furthermore, the storing unit F3 operates to store skeleton image data in a memory, the detecting unit F4 is in charge of positional detection of images acquired at time instants tn and tn−1, which are subjected to subtraction, and the difference extraction unit F5 performs the subtraction between two frames of skeleton data. The processing unit F6 is in change of calculation of collimating openings and detection of moving speeds of the C-shaped arm 13.

Figure 13:
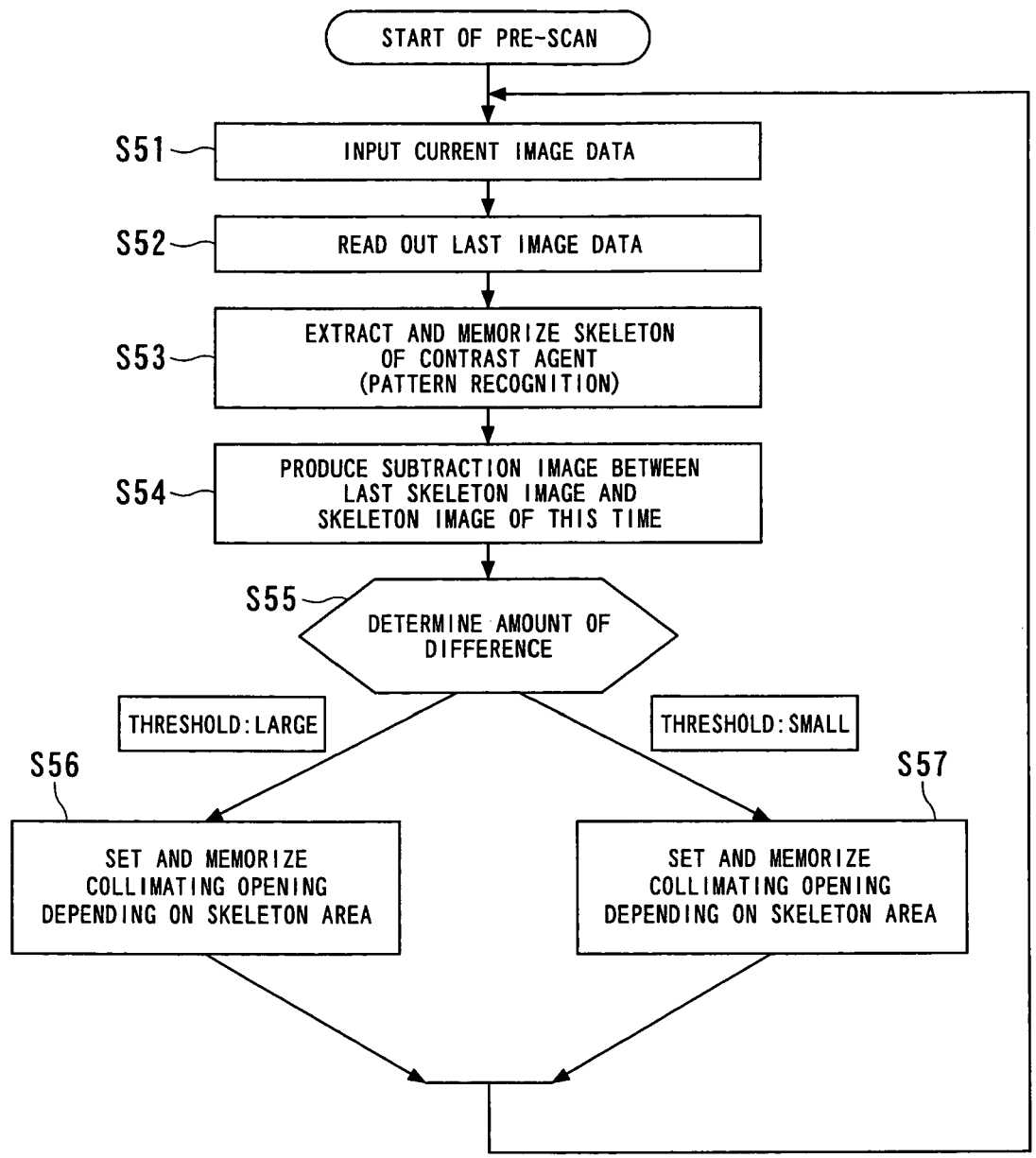
FIG. 13 is a flow chart outlining an example for automatically setting collimating openings of the X-ray collimator at respective imaging positions, the setting processing being performed by the skeleton processor.
Figure 14:
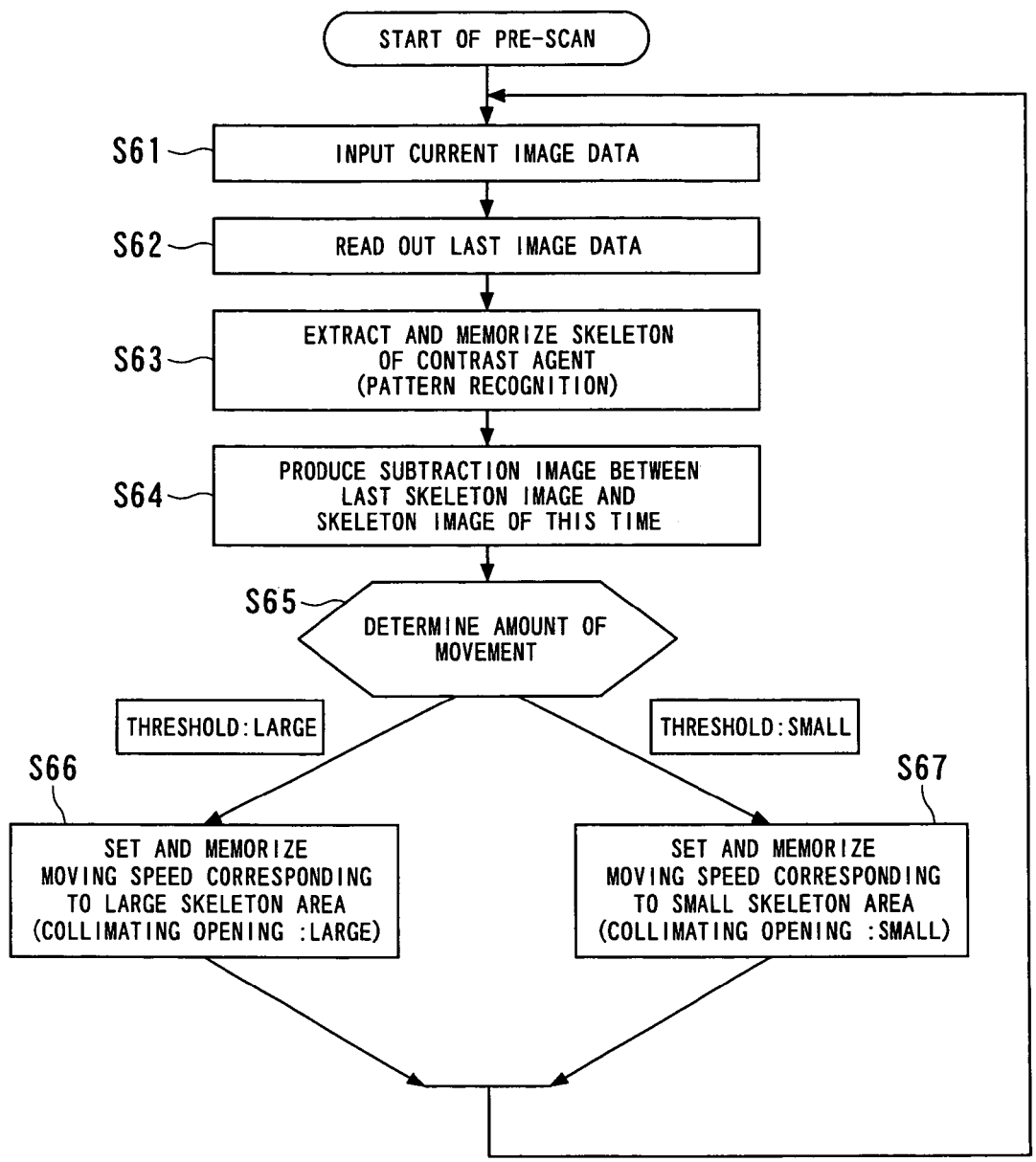
FIG. 14 is a flow chart outlining an example for automatically setting movement speeds of the C-shaped arm at respective imaging positions, the setting processing also being performed by the skeleton processor.

More specifically, the skeleton processor 70 is configured to execute the processing shown in each of FIGS. 13 and 14, for example, in a time sharing manner during the performance of a pre-scan (i.e., preparation scan). The processing in FIG. 13 shows the procedures for determining collimating openings of the X-ray collimator 21, while the processing in FIG. 14 shows the procedures for determining relative moving speeds of one of the C-shaped arm 13 and the tabletop 15 to the other (in the present embodiment, the C-shaped arm is moved with the tabletop 15 in position). As an alternative way, the skeleton processor 70 may execute only either the processing in FIG. 13 or the processing in FIG. 14.

The skeleton processor 70 inputs the data of images acquired at a certain imaging position (plural sampling timings tn) from the image data storage 60 through the system controller 51, the image data being acquired under the current pre-scan (step S51). The skeleton processor 70 then reads out, from its internal image data memory image, data of a skeleton of the contrast agent, which were acquired at the last imaging position (plural sampling timings tn−1) and already processed (step S52).

The skeleton processor 70 performs the extraction of a skeleton, the production of a difference image, and the determination of a collimating opening, in sequence.

To be specific, first of all, a skeleton of the X-ray contrast agent at the certain imaging position subjected to the plural sampling timings tn is extracted by performing differential processing (recognized as a pattern), and then the image data at the pixels of the skeleton is temporarily stored in the internal memory (step S53). Then, the skeleton images at both of the imaging positions (sampling timings tn and tn−1) undergo subtraction, pixel by pixel, so that a difference image is produced (step S54). This production of the difference image is pictorially shown in FIG. 15.

Then the data of the difference image is subjected to calculation of an amount of difference (i.e., an area of difference) and it is determined whether or not the amount of difference is equal to or more than a predetermined threshold (step S55). If the amount of difference is equal to or more than the predetermined threshold, a collimating opening of the X-ray collimator 21 which depends on the amount of difference, that is, an area of the skeleton is determined with reference to, for example, a first data table previously set, thereby data indicative of the determined collimating opening being stored into the internal memory (step S56).

On the other hand, if the amount of difference is less than the predetermined threshold, a collimating opening of the X-ray collimator 21 which depends on the amount of difference, that is, an area of the skeleton is determined with reference to, for example, a second data table previously set differently from the first data table, thereby data indicative of the determined collimating opening being stored into the internal memory (step S57). Applying the threshold processing to the amount of difference allows the collimating opening to be determined in detail and in a simple manner in dependence upon how fast the X-ray contrast agent flows.

When the collimating opening is decided in this way, image data acquired by the pre-scan at the next imaging position (plural sampling timings tn+1) is read out again (step S51), so that the foregoing processing is repeated.

Figure 15:
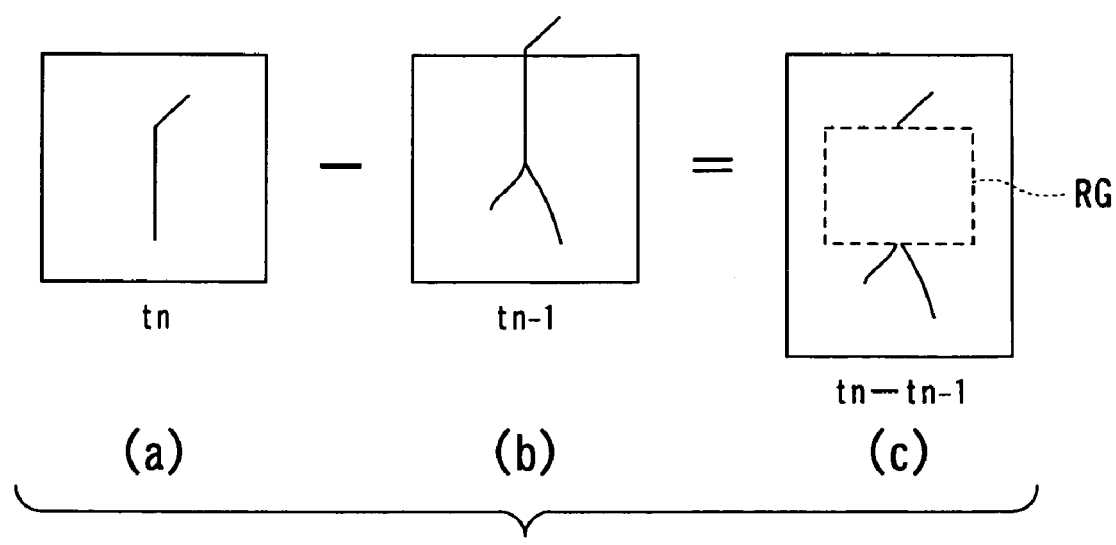
FIG. 15 is an explanation for automatically setting an opening of the X-ray collimator using extraction of skeletons of the X-ray contrast agent and subtraction thereof.
Figure 16:
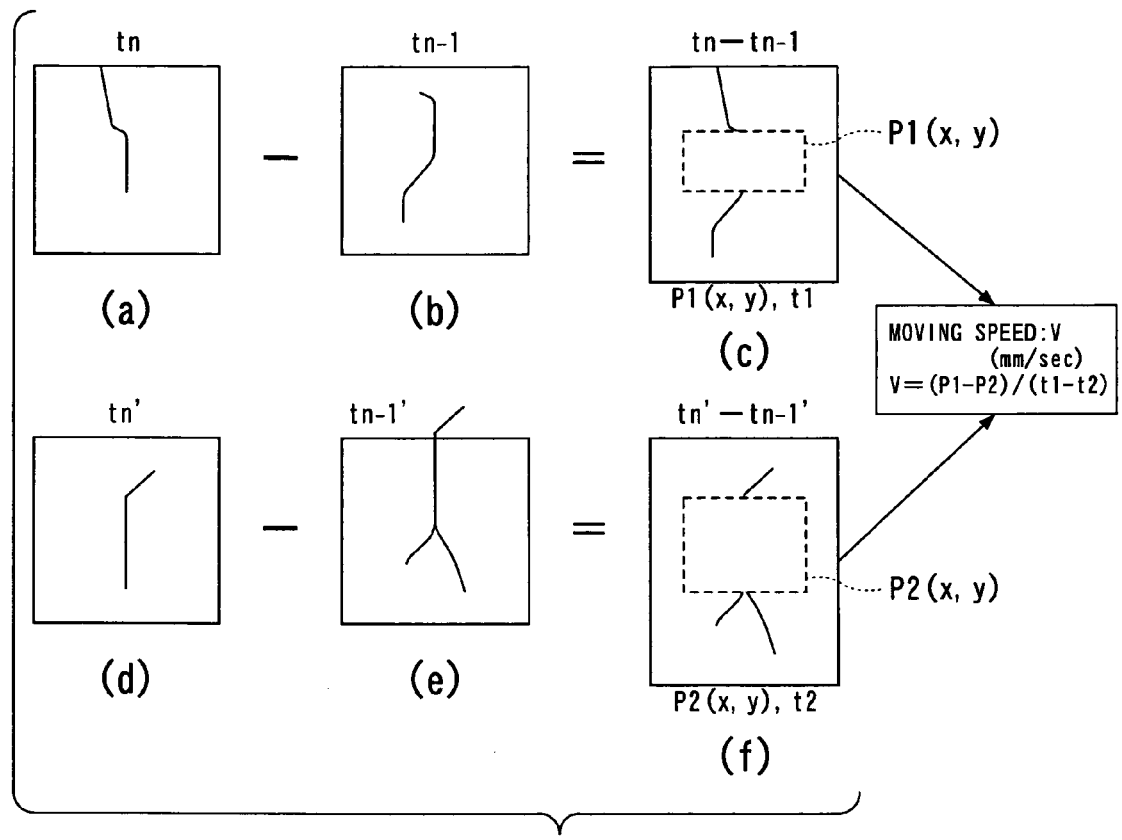
FIG. 16 is an explanation for automatically setting a movement speed of the C-shaped arm using extraction of skeletons of the X-ray contrast agent and subtraction thereof.

Therefore, during the execution of the pre-scan, a fluoroscopic image acquired by the pre-scan under a planned sampling rate based on an experimental value is displayed in real time. The data of the fluoroscopic image is then subjected to differential processing to extract the skeleton of the X-ray contrast agent at respective imaging positions. Hence, a difference image between the skeleton images extracted at the current imaging position (plural sampling timings tn) and the last imaging position (plural sampling timings tn−1) is produced. How to produce the difference image is pictorially exemplified in FIG. 15($a$) to ($c$). Based on this difference image, a collimating opening at a certain imaging position (as shown in FIG. 15($c$), in which a region RG enclosed by a dashed line shows an optimum collimating opening) can be decided and a flow speed of the X-ray contrast agent can be calculated.

Meanwhile, as shown in FIG. 14, the skeleton processor 70 inputs the data of images acquired at a certain imaging position (plural sampling timings tn) from the image data storage 60 through the system controller 51, the image data being acquired under the current pre-scan (step S61). The skeleton processor 70 then reads out, from its internal image data memory image, data of a skeleton of the contrast agent, which were acquired at the last imaging position (plural sampling timings tn−1) and already processed (step S62).

The skeleton processor 70 performs the extraction of a skeleton, the production of a difference image, and the determination of a moving speed of the C-shaped arm 13, in sequence.

To be specific, first of all, a skeleton of the X-ray contrast agent at the certain imaging position subjected to the plural sampling timings tn is extracted by performing differential processing (recognized as a pattern), and then the image data at the pixels of the skeleton is temporarily stored in the internal memory (step S63). Then, the skeleton images at both of the imaging positions (at sampling timings tn and tn−1) undergo subtraction, pixel by pixel, so that a difference image is produced (step S64). This production of the difference image is pictorially shown in FIG. 16.

Then the data of the difference image is subjected to calculation of an amount of movement of the X-ray contrast agent, and it is determined whether or not the amount of movement is equal to or more than a predetermined threshold (step S65). If the amount of movement is equal to or more than the predetermined threshold, a moving speed of the C-shaped arm 13 which depends on a larger skeleton area (a larger collimating opening) is determined with reference to, for example, a third data table previously set, thereby data indicative of the determined moving speed being stored into the internal memory (step S66).

On the other hand, if the amount of movement of the contrast agent is less than the predetermined threshold, a moving speed of the C-shaped arm 13 which depends on a smaller skeleton area (a smaller collimating opening) is determined with reference to, for example, a fourth data table previously set differently from the third data table, thereby data indicative of the determined moving speed being stored into the internal memory (step S67). Applying the threshold processing to the amount of movement allows the moving speed of the C-shaped arm 13 to be determined in detail and in a simple manner in dependence upon how fast the X-ray contrast agent flows.

When the collimating opening is decided in this way, image data acquired by the pre-scan at the next imaging position (plural sampling timings tn+1) is read out again (step S61), so that the foregoing processing is repeated.

Therefore, during the execution of the pre-scan, a fluoroscopic image acquired by the pre-scan under a planned sampling rate based on an experimental value is displayed in real time. The data of the fluoroscopic image is then subjected to differential processing to extract the skeleton of the X-ray contrast agent at respective imaging positions. Hence, a difference image between the skeleton images extracted at this time of imaging position (plural sampling timings tn) and the last imaging position (plural sampling timings tn−1) is produced. How to produce the difference image is pictorially exemplified in FIGS. 16(a) to (c) (d) to (f).

From these difference images, a collimating opening at a certain imaging position (a representative imaging time t1) can be decided, for example, as shown by a region P1(x, y) enclosed by a dashed line in FIG. 16(c)) and the other collimating opening at the next imaging position (a representative imaging time t2) can be decided, for example, as shown by a region P2(x, y) enclosed by a dashed line in FIG. 16(f)) (steps S65 and S66 in FIG. 14).

Hence a change in the positions of the collimating openings realized when the C-shaped arm 13 is moved from a certain imaging position (at a representative imaging time t1) to the next imaging position (at a representative imaging time t2), that is, a speed V (mm/sec) at which the C-shaped arm 13 should move (referred to as a moving speed of the C-shaped arm 13) is given by the following formula:

$$V=(P1-P2)/(t1-t2) \qquad (2),$$

which is calculated at steps S65 and S66 of the processing shown in FIG. 14, respectively. The data of the calculated moving speed V of the C-shape arm 13 is stored into the imaging parameter storage 64.

As stated above, like the imaging scan in the foregoing first embodiment, the imaging parameters necessary for the imaging scan are stored in the imaging parameter storage 64. Hence when the imaging scan is carried out, the imaging parameter controller 65 is allowed to read out the imaging parameters, and used in the imaging scan. That is, the collimating opening of the X-ray collimator 21 is automatically adjusted according to its data predetermined every imaging region (position) using the fluoroscopic image acquired by the pre-scan and each imaging region is subject to the imaging scan at a desired frame rate "f" and a desired imaging interval "K" between imaging positions, so that the C-shaped arm 13 is moved to the next imaging region (position) follow the flow of the X-ray contrast agent.

Accordingly, in the second embodiment, the pre-scan provides a fluoroscopic image, during which time the skeletons of the flow of the X-ray contrast agent are recognized as patterns, and collimating openings are obtained almost in real time from information about the recognized patterns and stored in the imaging parameter storage 64. Responsively to this, the imaging parameter controller 65 reads out the information about the collimating openings from the imaging parameter storage 64 and sends them to the X-ray collimating controller 55 via the system controller 51. This allows the collimating opening of the X-ray collimator 21 to be adjusted to each value specified by the X-ray collimating controller 55 almost in real time during the pre-scan. It is therefore possible that, at each imaging region (position), the X-rays are prevented from being radiated onto a portion of the imaging region from which the X-ray contrast agent has already flowed out, resulting in that an amount of X-ray exposure to the object can be lessened in response to the prevention.

In general, the flow speed of blood in a lesion, that is, the flow speed of the X-ray contrast agent is slower. Hence, as described in this second embodiment, using the automatic trace function of the contrast agent skeletons makes it possible that the collimating opening of the X-ray collimator 21 is set to a narrow value at the imaging region including the lesion. An imaging region (position) including the lesion can be determined by assigning the thresholds used in the determination of the amounts of difference and/or movement in FIGS. 13 and/or 14 to proper values based on, for example, experimental results.

In addition, when information about both of the past determined difference/movement amounts based on the thresholds and the imaging positions are used, how fast the X-ray contrast agent flows from now on can be estimated, and information indicating the estimated results can be memorized as part of the imaging parameters. It is possible to apply this estimated information to control of the opening of the X-ray collimator and the movement of the C-shaped arm under the imaging scan. The imaging parameters under the imaging scan can also be controlled with more accuracy. The processing for the estimation is executed by, for instance, the skeleton processor 70.

Moreover, in the second embodiment, the fluoroscopic image produced by the pre-scan is used for the pattern recognition of the contrast agent skeletons. The information resulting from the pattern recognition is the determination of the imaging parameters, such as the opening of the X-ray collimator 21, the flow speed of the X-ray contrast agent, the moving speed of the C-shaped arm 13, at each imaging position under the imaging scan. The determined imaging parameters are automatically memorized into the imaging parameter storage 64. Hence, unlike the first embodiment, there is no necessity for operator's manual setting of the imaging parameters at each imaging position on the fluoroscopic image. The aid for the operator's operation is thus remarkably strengthened, so that the operator's work is lessened to a great extent.

When the imaging scan is performed, the foregoing automatically set imaging parameters are read out under the control of the imaging parameter controller 65, and automatically sent to both the X-ray collimating controller 55 and the support-apparatus controller 57 via the system controller 51. For the imaging scan, the imaging parameters automatically set on the fluoroscopic image acquired in the pre-scan are used in the same manner as that in the first embodiment, in which the imaging scan is carried out with both the collimating opening and the C-shaped arm moving speed adjusted in an automatic fashion.

As a result, it is not necessary for the operator to manually operate the movement of the C-shaped arm, thereby the operator can be made free from such a time-consuming and cumbersome operation. The operator is thus able to concentrate on diagnosis on an image displayed under the imaging scan. An operational burden on the operator is thus alleviated remarkably and a throughput for examinations is increased because of improved operational efficiency.

Additionally to the above operational advantages, the installment of the dead man's switch 71 ensures the occurrence of emergency cases is treated in a sure manner. As long as the operator pushes down the dead man's switch 71, this X-ray diagnostic system is permitted to work in its normal conditions. On the other hand, when abnormal states occur concerning the X-ray tube, C-shaped arm, tabletop and others, the operator stops operating (pushing) the dead man's switch 71, which has been pushed so far, thus making it possible to avoid such abnormal states immediately.

Some modifications with regard to the foregoing embodiments can still be provided. The foregoing embodiments have employed the X-ray detector 30 equipped with the I.I. 31 and the TV camera 32 combined by the optical system 33, but this is not a definitive list. For example, a semiconductor-array flat panel detector (FPD) for detecting the X-ray can be employed as well, in which electrical circuitry composed of switching elements, capacitors and others which are formed on a glassmade substrate is covered by a photo-electric film to covert radiation rays to electric charges. In this case, both the I.I. controller 58 and the TV camera controller 59 are replaced with an FPD controller to control the FPD.

Additionally, instead of the foregoing embodiment configuration in which the tabletop 15 is kept without any movements with the C-shaped arm 13 moved to carry out the X-ray imaging, the C-shaped arm 13 can be made stationary if the tabletop 15 is moved for the X-ray imaging. Moreover, if necessary, both the C-shaped arm 13 and the tabletop 15 can be moved to produce a relative movement therebetween.

The present invention is not restricted to the constructions shown in the foregoing embodiments, but a person having ordinary skill in the art can create a variety of constructions adequately altered or deformed within the scope of the claims.

What is claimed is:

1. An X-ray diagnostic system comprising:
    an X-ray source irradiating an X-ray;
    an X-ray detector detecting the X-ray;
    a support apparatus configured to support both the X-ray source and the X-ray detector so that both the X-ray source and the X-ray detector are opposed to each other with a space left therebetween, a tabletop on which an object to be examined is laid being located in the space, the object being subjected to injection of an X-ray contrast agent when the object is examined;
    a fluoroscopic scan unit configured to relatively move one of the tabletop and the support apparatus with respect to the other and to perform a fluoroscopic scan along a direction predetermined with respect to the object with the one of the tabletop and the support apparatus relatively moved with respect to the other, the X-ray contrast agent flowing substantially along the direction, thereby a fluoroscopic image of the object being provided along the direction;
    an imaging parameter setting unit configured to set, at every region to be examined of the object, imaging parameters required for an imaging scan on the basis of the fluoroscopic image, the regions being at least continuous without a gap along the direction determined with respect to the object, the imaging parameter setting unit comprising means for setting, as one of the imaging parameters, a relative moving speed of the one of the tabletop and the support apparatus with respect to the other depending on a speed of the X-ray contrast agent flowing in the object, including means for producing a difference image of two images of said object containing said X-ray contrast agent at two different positions in said object and determining an amount of movement of said X-ray contrast agent using said difference image; and
    an imaging scan unit configured to relatively move the one of the tabletop and the support apparatus with respect to the other and, with the one of the tabletop and the support apparatus relatively moved with respect to the other, perform the imaging scan on the object according to the imaging parameters set by the imaging parameter setting unit, the imaging scan unit including means for controlling a radiation field of the X-ray on the object in the direction depending upon the moving speed and the imaging parameters.

2. An X-ray diagnostic system according to claim 1, wherein the imaging parameter setting unit is configured to accept information inputted by an operator's manual operation and to set the imaging parameters in response to the operator's manually operated information.

3. An X-ray diagnostic system according to claim 1, wherein the imaging parameter setting unit comprises means for setting, as one of the imaging parameters, a frame rate required for the imaging scan depending on a speed of the X-ray contrast agent flowing in the object, wherein
    the radiation field controlling means is configured to control the radiation field in dependence upon the frame rate.

4. An X-ray diagnostic system according to claim 1, further comprising a region specifying unit configured to specify a specific region of the object, wherein
    the radiation field controlling means comprises means for controlling the radiation field to an opening appropriate for imaging of the specific region in response to an arrival of a position of the imaging scan at the specific region.

5. An X-ray diagnostic system according to claim 1, wherein the imaging parameter setting unit is configured to, from the fluoroscopic image obtained by the fluoroscopic scan unit, automatically recognize the region through which the X-ray contrast agent flows and to set the imaging parameters based on a recognized result of the automatic recognition.

6. An X-ray diagnostic system according to claim 5, wherein the imaging parameter setting unit comprises means for automatically calculating, using a pattern recognition technique, the X-ray-contrast-agent flowing regions from the fluoroscopic image and means for setting, as part of the imaging parameters, region by region, an X-ray collimating opening depending on the X-ray-contrast-agent flowing regions based on a calculated result of the calculating means,
    wherein the imaging scan unit comprises means for controlling an X-ray collimator in compliance with the X-ray collimating opening.

7. An X-ray diagnostic system according to claim 5, wherein the imaging parameter setting unit comprises means for automatically calculating, using a pattern recognition technique, the X-ray-contrast-agent flowing regions from the fluoroscopic image and means for setting, as part of the imaging parameters, region by region, a relative moving speed of one of the tabletop and the support apparatus with respect to the other depending on a flowing speed of the X-ray contrast agent based on a calculated result of the calculating means,
    wherein the imaging scan unit comprises means for controlling the relative speed of the one of the tabletop and the support apparatus with respect to the other.

8. An X-ray diagnostic system according to claim 5, wherein the imaging parameter setting unit comprises means for automatically calculating, using a pattern recognition technique, the X-ray-contrast-agent flowing regions from the fluoroscopic image and means for setting, as part of the imaging parameters, region by region, an X-ray collimating opening and a relative moving speed of one of the tabletop and the support apparatus with respect to the other depending on a flowing speed of the X-ray contrast agent based on a calculated result of the calculating means,
    wherein the imaging scan unit comprises means for controlling an X-ray collimator in compliance with the X-ray collimating opening and means for controlling the relative speed of the one of the tabletop and the support apparatus with respect to the other.

9. An X-ray diagnostic system according to claim 5, further comprising:
    a calculation unit configured to automatically calculate, using a pattern recognition technique, the X-ray-contrast-agent flowing regions from the fluoroscopic image obtained by the fluoroscopic scan unit; and a control unit configured to automatically and in real time control a radiation field of the X-ray onto the object on the basis of a calculated result of the calculation unit, the X-ray being radiated from the X-ray source during acquisition of the fluoroscopic image provided by the fluoroscopic scan unit.

10. An X-ray diagnostic system according to claim 1, wherein:
said means for producing a difference image comprises a processor and a memory;
said memory storing images of said object containing said contrast agent;
said processor being programmed to read out said images, subtract a first image from a second image to produce said difference image, determine an amount of movement using said difference image, comparing said amount of movement to a threshold value, and determining said moving speed based upon whether said movement amount is less than or at least said threshold value.

11. An X-ray diagnostic system according to claim 10, wherein said processor is programmed to determine a first moving speed with reference to a first set of parameters when said movement amount is less than said threshold, and determine a second moving speed with reference to a second set of parameters when said movement amount is at least said threshold.

12. An X-ray diagnostic system according to claim 11, wherein said processor is programmed to:
determine said first position P1 at a first imaging time t1;
determine said second position P2 at a second imaging time t2; and
determine said moving speed as P1−P2/t1−t2.

13. An X-ray diagnostic system according to claim 10, wherein said processor is programmed to determine a first and second difference images, determine first and second positions in said first and second difference images, respectively, and determine a moving speed using said first and second positions.

14. A method of X-ray imaging performed by an X-ray diagnostic system comprising an X-ray source irradiating an X-ray; an X-ray detector detecting the X-ray; and a support apparatus configured to support both the X-ray source and the X-ray detector so that both the X-ray source and the X-ray detector are opposed to each other with a space left therebetween, a tabletop on which an object to be examined is laid being located in the space, the object being subjected to injection of an X-ray contrast agent when the object is examined,
the method comprising the steps of:
relatively moving one of the tabletop and the support apparatus with respect to the other and performing a fluoroscopic scan along a direction predetermined with respect to the object with the one of the tabletop and the support apparatus relatively moved with respect to the other, the X-ray contrast agent flowing substantially along the direction, thereby a fluoroscopic image of the object being provided along the direction;
producing a difference image of two images of said object containing said X-ray contrast agent at two different positions of said object;
determining an amount of movement of said X-ray contrast agent using said difference image;
setting, at every region to be examined of the object, imaging parameters required for an imaging scan on the basis of the fluoroscopic image, the regions being at least continuous without a gap along the direction determined with respect to the object, the imaging parameters including a relative moving speed of the one of the tabletop and the support apparatus with respect to the other depending on a speed of the X-ray contrast agent flowing in the object; and
relatively moving the one of the tabletop and the support apparatus with respect to the other and, with the one of the tabletop and the support apparatus relatively moved with respect to the other, performing the imaging scan on the object according to the imaging parameters with controlling a radiation field of an X-ray on the object in the direction depending upon the moving speed and the imaging parameters.

15. An X-ray imaging method according to claim 14, comprising:
storing images of said object containing said contrast agent;
subtracting a first image from a second image to produce said difference image;
determining an amount of movement using said difference image;
comparing said amount of movement to a threshold value; and
determining said moving speed based upon whether said movement amount is less than or at least said threshold value.

16. An X-ray imaging method according to claim 15, comprising:
determining a first moving speed with reference to a first set of parameters when said movement amount is less than said threshold; and
determining a second moving speed with reference to a second set of parameters when said movement amount is at least said threshold.

17. An X-ray imaging method according to claim 15, comprising:
determining a first difference image;
determining a second difference image;
determining first and second positions in said first and second difference images, respectively; and
determining a moving speed using said first and second positions.

18. An X-ray imaging method according to claim 17, comprising:
determining said first position P1 at a first imaging time t1;
determining said second position P2 at a second imaging time t2; and
determining said moving speed as P1−P2/t1−t2.

* * * * *